(12) United States Patent
Ruzicka

(10) Patent No.: US 11,207,542 B1
(45) Date of Patent: Dec. 28, 2021

(54) PORTABLE WHOLE-BODY PHOTON THERAPY DEVICE

(71) Applicant: Evllve, LLC, Rexford, NY (US)

(72) Inventor: Robin Ruzicka, Rexford, NY (US)

(73) Assignee: Evllve, LLC, Rexford, NY (US)

( * ) Notice: Subject to any disclaimer, the term of this patent is extended or adjusted under 35 U.S.C. 154(b) by 0 days.

(21) Appl. No.: 16/909,916

(22) Filed: Jun. 23, 2020

(51) Int. Cl.
*A61N 5/06* (2006.01)

(52) U.S. Cl.
CPC ........ *A61N 5/06* (2013.01); *A61N 2005/0638* (2013.01); *A61N 2005/0652* (2013.01); *A61N 2005/0659* (2013.01); *A61N 2005/0663* (2013.01)

(58) Field of Classification Search
CPC .............. A61N 5/06; A61N 2005/0652; A61N 2005/0659; A61N 2005/0663
See application file for complete search history.

(56) References Cited

U.S. PATENT DOCUMENTS

| | | | | |
|---|---|---|---|---|
| 6,063,108 | A * | 5/2000 | Salansky | A61N 5/0616 606/13 |
| 7,311,722 | B2 * | 12/2007 | Larsen | A61N 1/40 607/88 |
| 7,559,945 | B2 * | 7/2009 | Breden | A61N 5/06 128/898 |
| 9,044,084 | B2 * | 6/2015 | Carter | A47B 47/0083 |
| 10,281,108 | B2 | 5/2019 | Guinn et al. | |
| 10,357,094 | B1 * | 7/2019 | Luu | A45D 29/00 |
| 2005/0004631 | A1 * | 1/2005 | Benedict | A61N 5/0619 607/88 |
| 2006/0206173 | A1 * | 9/2006 | Gertner | A61N 5/0616 607/88 |
| 2011/0121654 | A1 * | 5/2011 | Recker | H02J 7/0068 307/66 |

(Continued)

OTHER PUBLICATIONS

"Oakworks The BOSS Treatment Table Packages from MassageKing" (Wayback Machine: https://web.archive.org/web/20140706232142/http://www.massageking.com/products/massage-table/Oakworks-The-BOSS-Treatment-Table-Packages/2538/1/1 PDF attached to office action, date captured: Jul. 6, 2014 (Year: 2014).*

(Continued)

*Primary Examiner* — Lynsey C Eiseman
*Assistant Examiner* — Amanda L Steinberg
(74) *Attorney, Agent, or Firm* — Carrie Stroup

(57) ABSTRACT

A portable photon therapy system is disclosed herein comprising a chassis, legs, headrest and footrest. When not in use, the legs can be folded, and the headrest and footrest detached and stored inside the chassis, which can be contained within a travel case. The device with case will comply with airline checked baggage requirements for size and weight. The chassis houses arrays of light-emitting diodes (LEDs) on printed circuit boards (PCBs) beneath an acrylic surface (device bed), which emit a plurality of light wavelengths at therapeutic irradiance levels. After device setup and upon selection of the desired light wavelengths (e.g. red or infrared or both) and mode (pulsed or continuous wave) via the control panel, one lays down on the device bed to undergo photon therapy. The present invention comprises a foldable 2-piece chassis for consumer photon therapy, and a single-piece chassis for patient photon therapy by medical professionals.

20 Claims, 12 Drawing Sheets

(56) References Cited

U.S. PATENT DOCUMENTS

| | | | |
|---|---|---|---|
| 2012/0150265 A1 | 6/2012 | Vargas et al. | |
| 2017/0165498 A1* | 6/2017 | Oversluizen | A61N 5/0625 |
| 2018/0147418 A1* | 5/2018 | Marchese | A61N 5/0625 |
| 2018/0236259 A1 | 8/2018 | Nelson et al. | |
| 2019/0142636 A1* | 5/2019 | Tedford | A61N 5/0613 606/4 |

OTHER PUBLICATIONS

Fedora Portable Massage Table Aluminum (only 27 lbs) from SpaandEquipment SkinAct on YouTube® published Nov. 19, 2015 [https://youtu.be/SBXnNx75pyI] (Year: 2015).*

Zein, R. et al. (2018) Review of light parameters and photobiomodulation efficacy: dive into complexity. J Biomed. Opt., 23(12), 120901: 1-17.

Hamblin MR. (2019) Photobiomodulation for Alzheimer's Disease: Has the Light Dawned? Photonics. 6(3):77.

Welch, D. et al. (2018) Far-UVC light: A new tool to control the spread of airborne-mediated microbial diseases, Scientific Reports, 8: 2752.

Wang Y. et al. (2017) Antimicrobial blue light inactivation of pathogenic microbes: State of the art. Drug Resist Update. 33-35:1-22.

Schuit, M. et al. (2020) The Influence of Simulated Sunlight on the Inactivation of Influenza Virus in Aerosols. The Journal of Infectious Diseases, 221(3): 372-378. Abstract only.

Rigonato-Oliveira, NC. et al. (2019) Effect of Low-Level Laser Therapy (LLLT) in Pulmonary Inflammation in Asthma Induced by House Dust Mite (HDM). Dosimetry Study. Int J Inflam. 3945496: 1-12.

Oliveira MC Jr, et al. (2014) Low level laser therapy reduces acute lung inflammation in a model of pulmonary and extrapulmonary LPS-induced. ARDS. J Photochem Photobiol B. 134:57-63. Abstract.

Brochetti, R.A. et al. (2017) Photobiomodulation therapy improves both inflammatory and fibrotic parameters in experimental model of lung fibrosis in mice. Lasers Med Sci, 32:1825-1834.

Lutai, A.V. (2001) Laser therapy of elderly patients with pneumonia. Vopr Kurortol Fizioter Lech Fiz Kult 3: 15-18. Abstract.

Ostronosova NS. (2006) Outpatient Use of Laser Therapy in Bronchial Asthma. Ter Arkh. 78(3):41-44. Abstract.

Milojević M. et al. (2003) Low power laser biostimulation in the treatment of bronchial asthma. Med Pregl. 56(9-10):413-418. Abstract.

Dabbous OA. et al. (2017) Evaluation of the improvement effect of laser acupuncture biostimulation in asthmatic children by exhaled inflammatory biomarker level of nitric oxide. Lasers Med Sci. 32(1):53-59. Abstract.

Enwemeka, C.S. et al. (2020) Light as a potential treatment for pandemic coronavirus infections: A perspective. Journal of Photochemistry & Photobiology, B: Biology, 1-27.

* cited by examiner

PORTABLE WHOLE-BODY PHOTON THERAPY DEVICE

FIELD OF THE INVENTION

The present disclosure is in the field of healthcare devices. More particularly, the present disclosure describes a lightweight, portable device for providing whole-body photon therapy with detachable headrest and footrest stowable in a chassis, thereby facilitating placement in a travel case for transportation.

BACKGROUND

Photon therapy, also referred to phototherapy and heliotherapy, can be used to modulate cells, which is referred to as photobiomodulation, or to inactivate pathogens, such as viruses and bacteria.

Photobiomodulation therapy (PBMT) refers to the modulation (stimulation or inhibition) of numerous cell types (muscle, neural, macrophage, fibroblast, osteoblast, adipose) via photons (light) from low-level lasers or light emitting diodes (LEDs).

An excess of a thousand research articles covering more than fifty years describe factors such as wavelength, irradiance, fluence, energy, power, mode (pulse or continuous), duration, and repetition, that support positive results from PBMT usage (Zein et al., 2018 [1]). Central to understanding of any of these results may be the Arndt-Shultz law which states "for every substance, small doses stimulate, moderate doses inhibit, and large doses kill". Hormesis, which is based on this law, is defined as "any process in a cell or organism that exhibits a biphasic response to exposure to increasing amounts of a substance or condition". In PBMT research, the favorable hormetic zone is typically discerned via a minimal and maximal dosage (fluence in $J/cm^2$) provided that effective wavelengths, mode (pulse or continuous), and irradiance ($mW/cm^2$) are utilized.

Research indicates that PBMT at an effective dose, within the hormetic zone, induces cascades of cellular reactions, which drive nitric oxide (NO) disassociation, briefly increase reactive oxygen species (ROS), and increase adenosine triphosphate (ATP) (Hamblin, 2019 [2]). Ultimately the pathways, transcription factors and growth factors activated through the reactions may facilitate endurance, strength, and recovery for users.

Photon therapy can also be used to inactivate viruses and bacteria using a similar dose (fluence in $J/cm^2$) driven approach as PBMT provided that effective wavelengths, mode (pulse or continuous), and irradiance ($mW/cm^2$) are utilized. While ultra-violet (UV) light has been known to kill bacteria since the late 1800's, it has some well-known detrimental effects on skin health. Very recent research suggests, a subset of this wavelength range, Far-UVC, shows similar efficacy for inactivation of pathogens but with potentially less risk of skin damage (Welch et al., 2018 [3]). Beyond UV light, blue and violet light have shown effectiveness in the inactivation of a wide variety of pathogens (Wang et al., 2017 [4]). and (Schuit et al., 2020 [5]). While the exact mechanism of pathogen inactivation, such as excessive ROS creation or loss of cellular membrane or capsid integrity, deserves further study, ultimately the pathogen inactivation enables one's immune system a better opportunity to defeat the associated diseases.

Whole-body photon therapy devices in the prior art may resemble tanning beds. Such devices may weigh over 250 pounds, often require 220V or 240V circuit, and are not easily transportable due to size and weight. Airline weight and size restrictions and vehicle trunk space limitations make transportation of such whole-body devices challenging.

Vertically mounted photon therapy devices in the prior art can irradiate a significant surface area of one's body; but these devices are not practical for transportation for the same size and weight reasons. Also, being vertically mounted necessitates that one has to stand to use the device, which may be problematic as treatment duration may be up to 30 minutes per side to obtain therapeutic results.

What is needed within the photon therapy industry is a lightweight, portable device, which allows for quick assembly, usage, and storage. For PBMT, the device should allow one to undertake effective (within the hormetic zone) and efficient (not more than 30 minutes per session total) therapy while traveling, such as for many athletes who spend a significant portion of their career on the road and away from home. For inactivation of pathogens, the portable device should be able to be quickly setup when and where needed by medical practitioners and staff for effective and efficient treatment of patients using prescribed dosages.

SUMMARY

The present invention relates to a whole-body photon therapy device in a novel horizontal design, and which is portable, lightweight, and runs on universal power from 110V to 240V. This is a major improvement to whole-body photon therapy devices as it allows for practical transport of the device, which meets major airline checked baggage weight and size restrictions, while still enabling photon therapy at therapeutic wavelengths and irradiance levels. The device's main components include a horizontal chassis with foldable legs and a hollow inner cavity to store the detachable headrest and footrest. The chassis fits inside a travel case.

The chassis houses a plurality of arrays of light-emitting diodes (LEDs) on printed circuit boards (PCBs) beneath an acrylic surface (device bed), which emit a plurality of light wavelengths at therapeutic irradiance levels. After device setup and upon selection of the desired light wavelengths (e.g. red light at 660 nm and infrared light at 850 nm) and mode (pulsed or continuous wave) via the control panel, one lays down on the device bed to undergo photon therapy.

In some embodiments, the photon therapy device is used primarily by consumers for photobiomodulation therapy (PBMT), and the device comprises a two-piece chassis which can be folded or disassembled for storage in a travel case. This lightweight and highly portable embodiment is particularly suited to consumers that travel frequently such as professional athletes.

In other embodiments, the photon therapy device is used primarily by medical professionals for patients undergoing PBMT, such as for treatment of inflammation due to COVID-19, or for pathogen inactivation. These embodiments comprise a single-piece chassis and the system is stored in a substantially rectangular shaped travel case.

The present invention further comprise a portable table housing a therapeutic photon therapy system and method of its use, comprising: a) a chassis comprising, one or two flat acrylic sheet(s), aligned end-to-end, positioned for a patient to lie down upon; four light-emitting diodes (LEDs) array printed circuit boards (PCBs) positioned in parallel beneath the flat acrylic sheet(s), wherein said LED array PCB houses a plurality of LEDs able to emit photons at a plurality of light wavelengths that pass through the acrylic sheet(s) and into the patient to provide a therapeutic or preventive treatment. The chassis further comprises: a control panel connected to a control PCB for entering and executing patient treatment protocols comprising: selection of light wavelengths, duration of treatment, and/or a mode of pulsed or continuous wavelengths; a power supply unit able to transmit current and/or voltage from a wall outlet to the control PCB. The chassis further comprises: a plurality of legs, wherein the legs are able to be folded into the chassis when device not in use; a headrest able to support one's head in both a supine and a prone position; and a footrest extending from an end of the chassis; and wherein the headrest and footrest are detachable from the chassis and able to be stored inside the chassis when the table is not in use.

The system further comprises one or more safety features, e.g. a) a least one thermal sensor positioned within each LED array PCB, able to shut off the LEDs when the PCB temperature exceeds a safety level; and/or b) an internal timer positioned within the control PCB, able to shut off the system after a set time duration to prevent over-exposure; and/or c) an emergency stop button on the control panel which disables the power supply unit. The system further comprises positioned beneath the four LED array PCBs, two driver PCB's, and four LED cooling blowers.

In an embodiment, the chassis comprises two acrylic sheets able to fold with the chassis in half to fit within a travel briefcase that meets an airline standard checked baggage requirements comprising 62 linear inches in total dimensions, and a maximum of 50 pounds. In another embodiment, the chassis comprises one acrylic sheet, and the chassis is stored in a substantially rectangular shaped travel case that meets an airline oversized/overweight checked baggage requirements comprising 126 linear inches in total dimensions, and a maximum of 100 pounds.

The LEDs emit therapeutic wavelengths between about 200 nm ultraviolet to about 1064 nm infrared, and at a therapeutic irradiance level between about 25 mW/cm$^2$ to about 100 mW/cm$^2$. The LEDs are arranged in an array pattern (e.g. rows, alternating red and IR lights, an array of just red lights or IR lights, etc.) to ensure delivery of a consistent irradiance and dosage.

The control panel further comprises two depress-able buttons for three operation options comprising: a primary wavelength (e.g. red light at 660 nm), a secondary wavelength (e.g. infrared light at 850 nm), or both primary and secondary (e.g. red and infrared light). In addition, the control panel further comprises a mode push button to enable one to select between pulsed or continuous wavelengths. In certain embodiments, the control panel also has timer functionality with push buttons to set duration and start timer, as well as a digital display. The present invention further comprises a non-transitory computer readable medium storing computer executable code, wherein the computer executable code, when executed by a processor on a mobile electronic computing device, is configured to: receive, transmit and display information between said mobile device and said chassis for controlling the operation of the system, comprising: a treatment time duration; a pulsed or continuous mode; and administration of a red light wavelength, a IR wavelength, or both.

BRIEF DESCRIPTION OF THE DRAWINGS

The above and other features, aspects, and advantages of the present disclosure will become better understood with regard to the following description, appended claims, and accompanying drawing herein.

DETAILED DESCRIPTION OF EXEMPLARY EMBODIMENTS

Figure 1A:
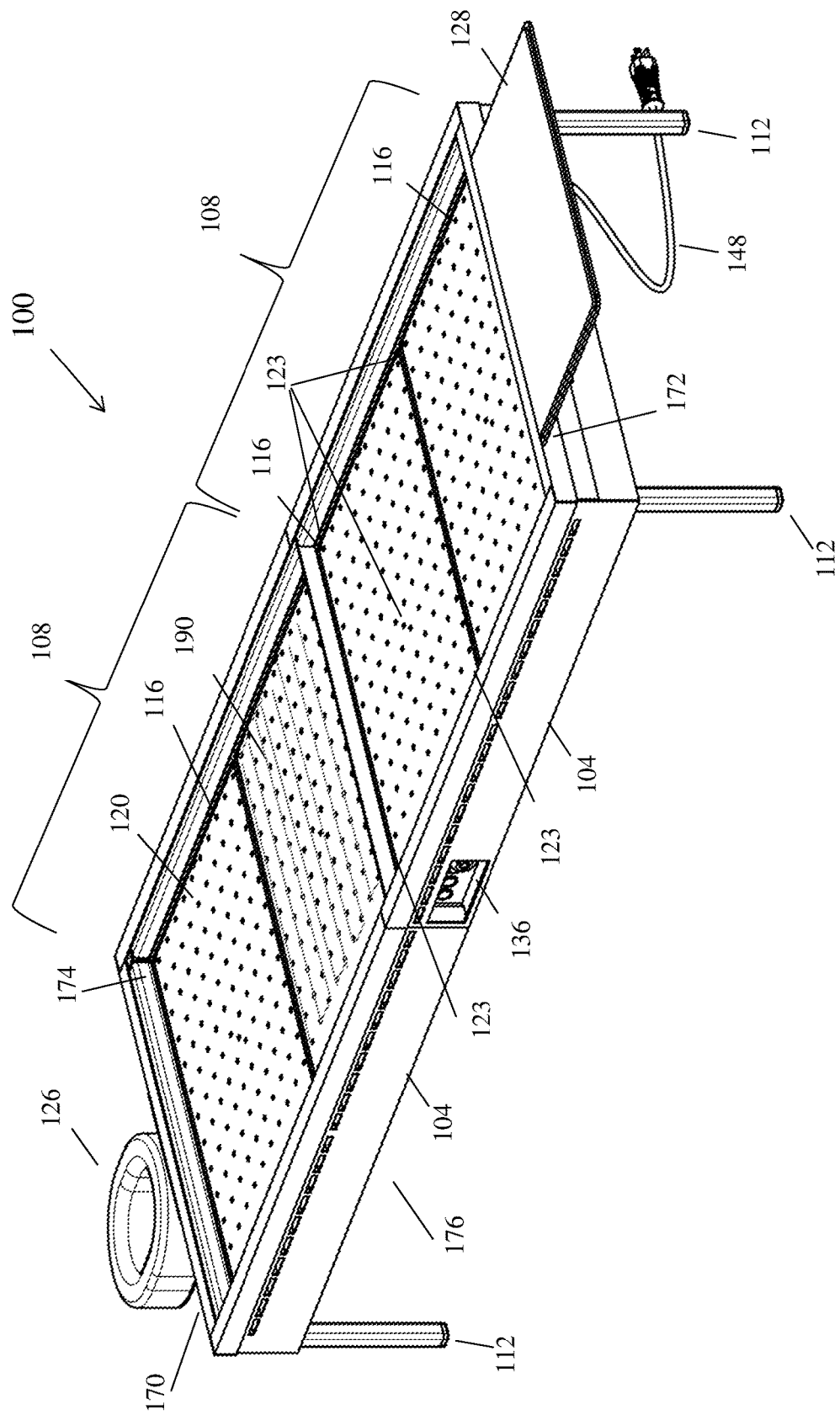
FIG. 1A is a perspective view of the photon therapy device in accordance with a two-piece chassis embodiment of the present disclosure.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As used herein, the term "photon therapy" refers to photobiomodulation, when pertaining to modulation of cells, and/or the inactivation of pathogens (viruses and bacteria).

As used herein, the term "photobiomodulation therapy (PMBT)" refers to the modulation (stimulation or inhibition) of numerous cell types (muscle, neural, macrophage, fibroblast, osteoblast, adipose) via photons (light) from light emitting diodes arranged in the device of the present invention.

As used herein, the term "system" refers to the photon therapy device (table) alone in an embodiment. In another embodiment, the term "system" refers to the photon therapy device and/or travel case and/or mobile application for controlling the chassis electronics.

As used herein, the term "Software" or "Computer Program Product" or "Mobile Application or App" refers to computer program instructions adapted for execution by a hardware element, such as a processor, wherein the instruction comprises commands that when executed cause the processor to perform a corresponding set of commands. The software may be written or coded using a programming language and stored using any type of non-transitory computer-readable media or machine-readable media well known in the art. Examples of software in the present invention comprise any software components, code, modules, programs, applications, computer programs, application programs, system programs, machine programs, and operating system software. The software, or computer program product is installed within memory on a computing device.

And although any methods, devices and materials similar or equivalent to those described herein can be used in the practice or testing of the present invention, some potential and preferred methods, devices, and materials are now described.

A whole-body photon therapy device is provided herein with a horizontal design which is portable, lightweight, and runs on universal power from 110V to 240V. The device allows for practical global transport (checked baggage weight and dimensions for air transport) of the device while still enabling photon therapy at therapeutic wavelengths and irradiance levels. Main components of the device include a chassis, a plurality of legs, as well as a headrest and a footrest.

In some embodiments, for consumer photobiomodulation therapy (e.g. treatment of muscle and joints and increasing blood circulation, such as for an athlete), the folded or disassembled two-piece chassis fits into a travel case that meets major airline standard checked baggage restrictions of 62 linear (length+width+height) total dimension inches (158 centimeters). In this embodiment, the entire system with travel case also meets major airline checked baggage weight restrictions of a maximum of 50 pounds (23 kilograms).

In other embodiments, for medical professionals delivering photon treatments (e.g. PBMT or inactivation of pathogens), the case and one-piece chassis would meet the airline oversized/overweight checked baggage restrictions of 126 linear (length+width+height) total dimension inches (320 centimeters) and the weight restrictions of a maximum of 100 pounds (45 kilograms).

The chassis houses a plurality of arrays of light-emitting diodes (LEDs) on printed circuit boards (PCBs) beneath an acrylic surface (device bed), which emit a plurality of light wavelengths at therapeutic irradiance levels under the operational control of a control panel. After device setup and upon selection of the desired light wavelengths and mode using the control panel (e.g. FIGS. 1-2B, 136) (i.e., red at 660 nm, infrared at 850 nm, and continuous wave or pulsed wave 145), one lays down on the device bed for a duration of time (based on treatment protocol) on each side (prone and supine) to undergo photon therapy.

Figure 1B:
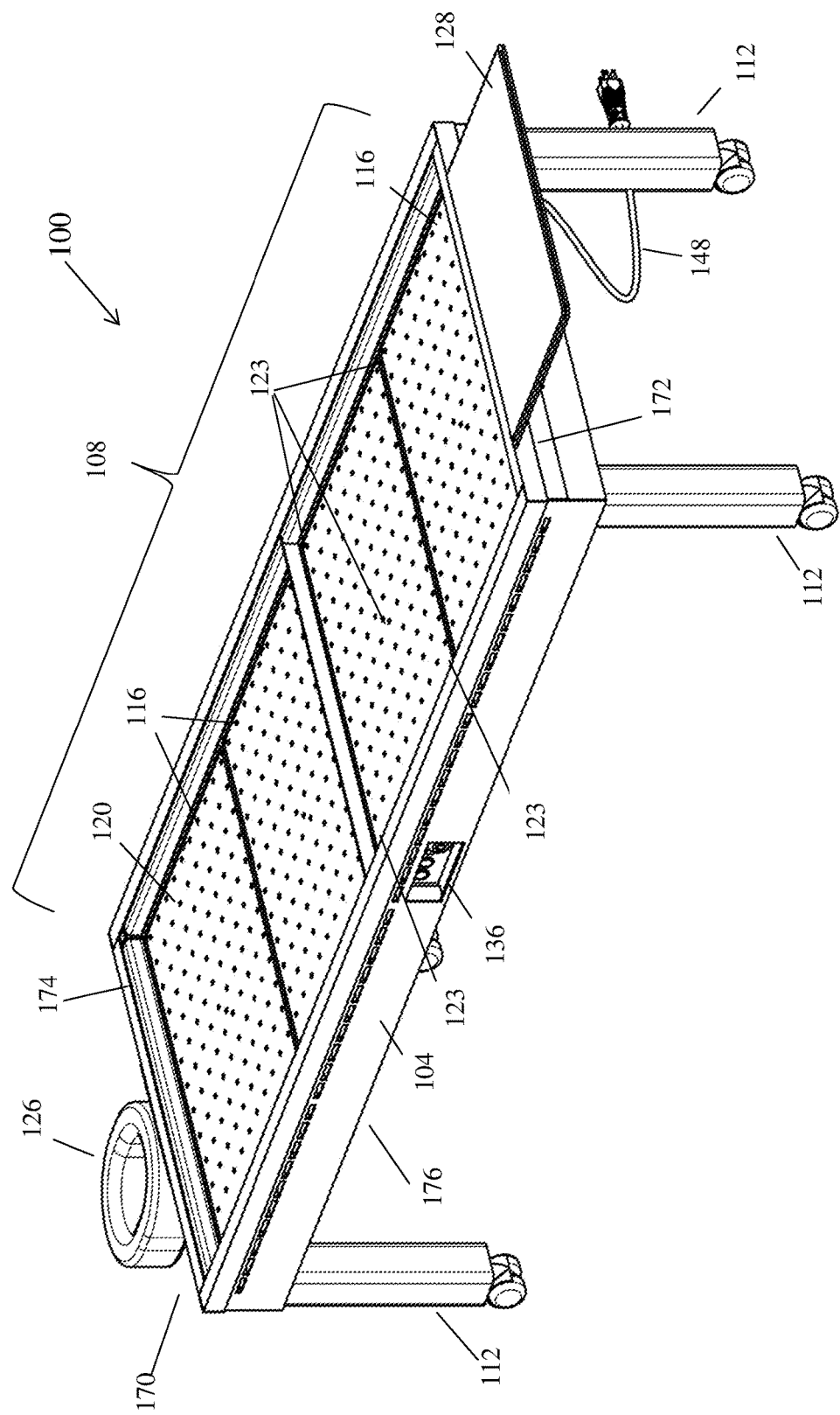
FIG. 1B is a perspective view of the photon therapy device in accordance with a single-piece chassis embodiment of the present disclosure.

Turning to the figures, FIGS. 1A and 1B are top perspective views of a whole-body portable photon therapy (phototherapy) device 100 enabling one to lay on top of the device bed and receive photon therapy. The modular design allows for quick disassembly of the device for storage and transport, with the main difference being that FIG. 1A chassis can be folded or disassembled.

The device may be used in an indoor and temperature-controlled environment so that it may be protected from inclement weather and overheating. This environment may be, by way of non-limiting examples: a home, a hotel room, a sports team facility, a medical facility, or a hospital.

FIGS. 1A and 1B illustrate components of a photon therapy device 100, hereafter referred to as "device 100" or "system 100", comprising: a chassis 104, a plurality of legs 112 (e.g. 4), a headrest 126, a footrest 128, and a power cord 148. Device 100 is substantially rectangular shaped with a front end 170, a rear end 172, a top surface 174, and a bottom surface 176.

FIG. 1A two-piece chassis 104 comprises two transparent acrylic sheets 108 (one sheet per chassis section), whereas FIG. 1B single-piece chassis 104 comprises a single transparent acrylic sheet 108. The acrylic sheet(s) 108 provide a horizontal flat top surface (device bed), substantially rectangular in shape, for one to lie upon.

Underneath the acrylic sheet(s) 108 are four substantially rectangular shaped LED Array printed circuit boards (PCB's) 116, aligned long end-to-short end (i.e. joining at the length side of the rectangular PCB 116). As used herein, "array" refers to the pattern of rows and columns of aligned light emitting diodes (LEDs) 120 arranged in string series 190 in each PCB 116. Other patterns of LEDs are envisioned for the device and depend upon the anatomical body part and/or injury type and/or medical condition being treated. Chassis 104 creates an enclosure for device electronics and LED Array printed circuit boards (PCBs) 116 upon which a plurality of light-emitting diode (LED) 120 are soldered. In an embodiment, LEDs 120 are positioned in altering rows or columns of red (660 nm) and IR (850 nm) LEDs, or violet (405 nm) and IR (850 nm) LEDs. In another embodiment, each LED 120 comprises a single emitter with multiple dies (e.g. one red and one IR or two violet and one IR) which can further optimize the consistency of device irradiance. The LEDs 120 can operate in continuous emission mode, or pulsed mode. These embodiments are only a few examples of the combination of device wavelengths whereas other embodiments will provide different therapeutic wavelengths for PMBT and pathogen inactivation.

Figure 8:
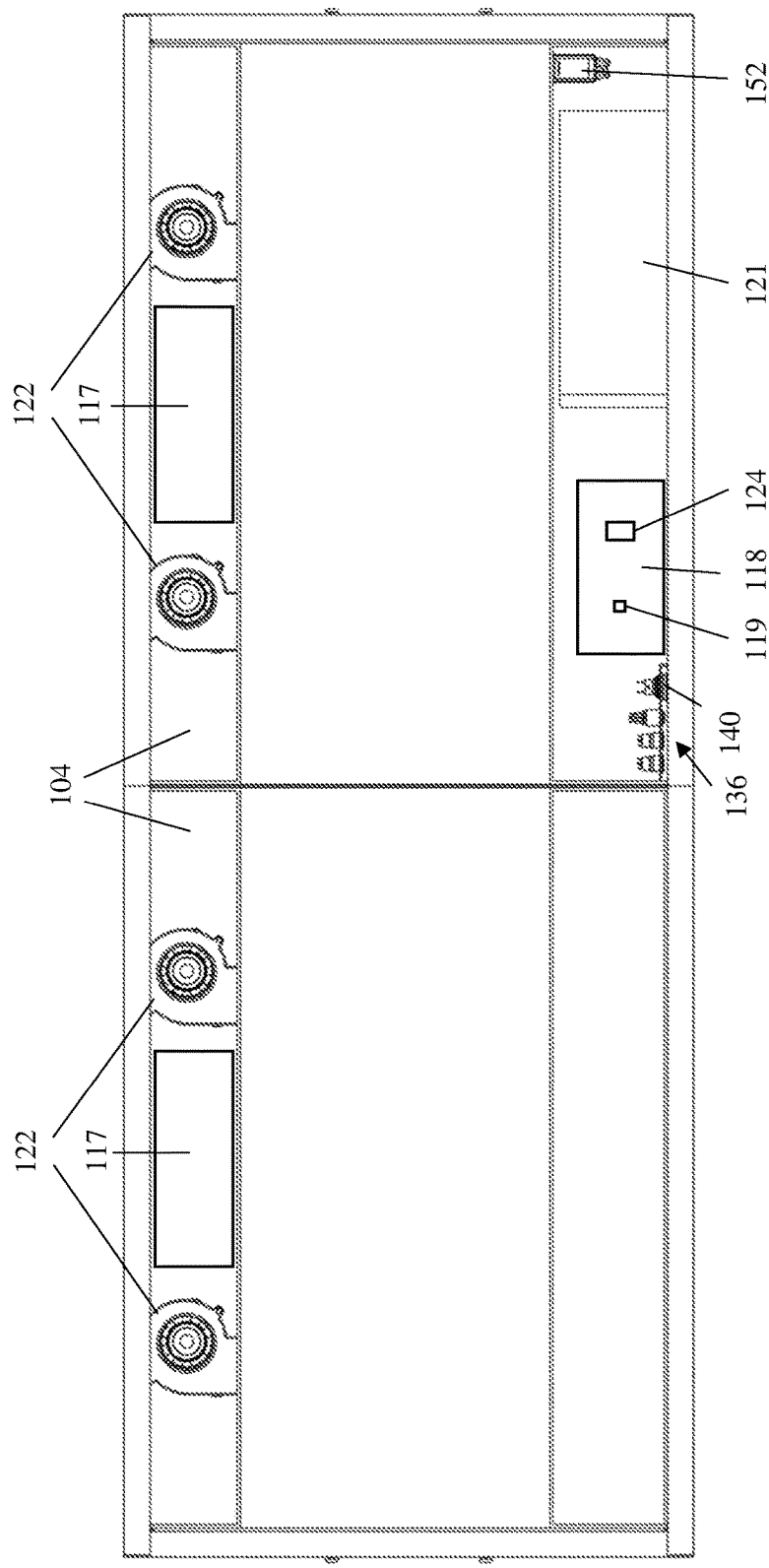
FIG. 8 is a longitudinal cross-sectional view of FIG. 4 taken along line 8-8, illustrating a cutaway view of the chassis, which shows the electronic components comprised within.

In an embodiment, the LED Array PCBs 116 may further comprise several thermal sensors 123 per PCB 116, such as one in each corner of the board 116 and in the center, to function as a safety feature to ensure the board does not overheat. Both pairs of PCBs 116 are under the operational control of a separate PCB 117 (as illustrated in FIG. 8).

The device 100 provides photon therapy through the utilization of the plurality of light-emitting diodes (LEDs) 120, either at continuous or pulsed emissions. The device is activated after plugging in the power cord 148 and adjusting the control panel 136 via buttons where one may activate different wavelengths of light and the mode of operation (continuous or pulsed). Next, one lays down on the acrylic sheet(s) 108 where one is exposed to the light from the LEDs 120, which is emitted through sheet(s) 108 so that one is not in direct contact with the LEDs 120; and thus undergoes photon therapy.

The modular design of device 100 allows for some components to be attached and detached from the chassis 104. The headrest 126 can be attached at the chassis front end 170 to provide support for one's head; and, the footrest 128 can be attached at the chassis rear end 172 to provide support for one's feet. This modular design factors into the portability of the device 100.

Headrest 126 comprises in an embodiment: an oval head pad, about 7×9×2 inches in dimensions, with oval hole in the middle and a thin support panel with a similar outline to the head pad with an L-bracket that facilitates attachment to the main chassis via slots.

Footrest 128 comprises in an embodiment: a thin rectangular panel, about 10×16 inches in dimensions, upon which a thin rectangular cushioned pad is adhered, and the panel has a L-bracket that facilitates attachment to the main chassis via slots.

The plurality of legs 112 comprises in an embodiment (FIG. 1A): about a 1-inch square tube that is about 10 inches in length with a small rubber end. Each leg 112 can fold into the chassis for storage and transport via a hinge mechanism (e.g. see FIG. 5). In another embodiment (FIG. 1B), the legs 112 will comprise about a 2-inch square tube about 12 inches in length with locking casters on the end to support mobility within a facility.

Figure 2B:
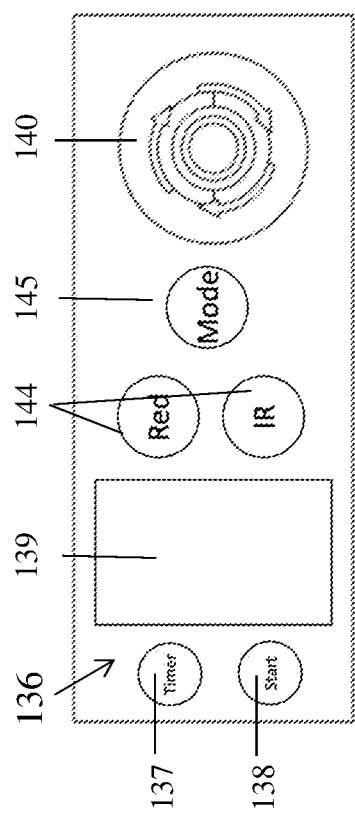
FIG. 2B is an illustration of another embodiment of the control panel of the photon therapy device further comprising a timer and a digital display that shows the time counting.
Figure 2A:
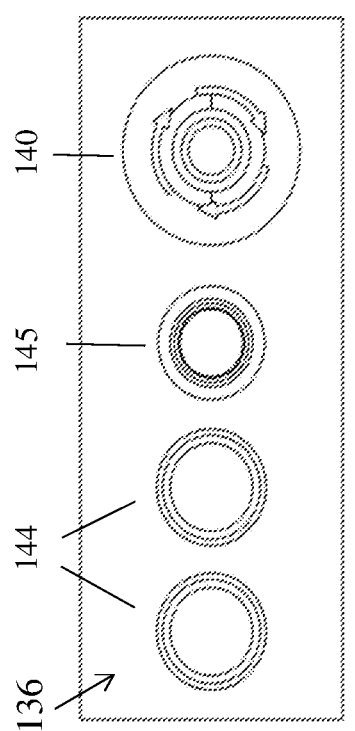
FIG. 2A is an illustration of one embodiment of the photon therapy device's control panel comprising: a push-button switch to control a pulsed or a continuous mode; and two LED wavelength switches.

FIGS. 2A and 2B are views of the control panel 136 in two different embodiments of the device, and they are located on the side of the chassis 104. In both embodiments, the control panel 136 comprises four illuminated switches or buttons. Control panel 136 contains an illuminated emergency off stop switch 140, which disables the power supply unit main power when pressed, powering down the Driver and Array PCBs, as well as the blowers. The control panel 136 also contains two illuminated pushbutton switches 144 for the control of LED wavelengths (e.g. one is red and one is infrared) which provides three wavelength options, either the first wavelength (e.g. red) or the second wavelength (e.g. IR) or both. Control panel 136 further comprises one illuminated pushbutton switch 145 for control of the mode. The LED wavelength switches 144 illuminate when active (e.g. the red switch illuminates when red wavelength emitting LED's 120 are on, and the blue switch illuminates when IR wavelength emitting LED's 120 are on). The mode switch 145 illumination pulsates in pulse mode and is constantly illuminated in continuous wave mode.

FIG. 2B also has two pushbuttons and one display panel which are enabled by a microcontroller (see FIG. 8, 124) on the Control PCB (see FIG. 8, 118). The control panel 136 contains a timer button 137 that increments the timer, a function of the microcontroller (see FIG. 8, 124) by 1 minute when pressed (until the maximum time is reached when it starts back at 1 minute). Pressing the start button 138 starts the timer and device where the remaining time is displayed on the digital display 139. Upon completion of the timer, the LEDs 120 are turned off.

Figure 2C:
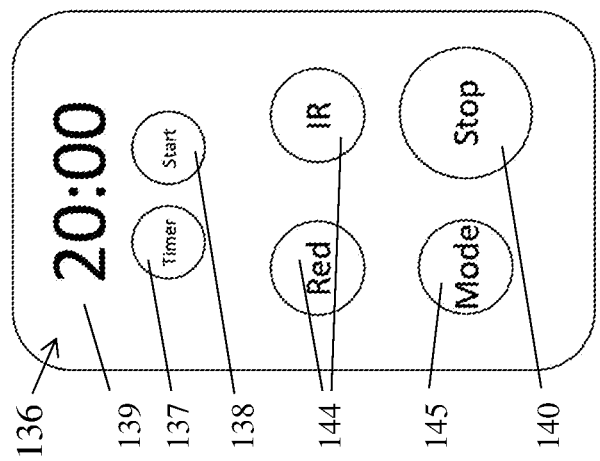
FIG. 2C is a view of the mobile phone application control panel of the photon therapy device in accordance with an embodiment of the present disclosure.

FIG. 2C is a view of the mobile phone application (software) control panel 136 for an which is enabled within an embodiment of the device 100 via the microcontroller (see FIG. 8, 124) on the Control PCB (see FIG. 8, 118). The mobile phone application (see FIG. 10, 200) has the same functionality as the FIG. 2B control panel (hardware) and mimics the design to keep the interface consistent. The control panel 136 has six button icons and a digital timer display 139. Control panel 136 contains an emergency off stop button 140, which disables the power supply unit main power when pressed, powering down the Driver and Array PCBs, as well as the blowers. The control panel 136 also contains two illuminated buttons 144 for the control of LED wavelengths (e.g. one is red and one is infrared) which provides three wavelength options, either the first wavelength (e.g. red) or the second wavelength (e.g. IR) or both. Control panel 136 further comprises one illuminated button 145 for control of the mode. The LED wavelength buttons 144 illuminate when active (e.g. the red switch illuminates when red wavelength emitting LED's 120 are on, and the blue switch illuminates when IR wavelength emitting LED's 120 are on). The mode button 145 illumination pulsates in pulse mode and is constantly illuminated in continuous wave mode. The control panel 136 also contains a timer button 137 that increments the timer by 1 minute when pressed (until the maximum time is reached when it starts back at 1 minute) which is displayed on the digital display 139. Pressing the start button 138 starts the timer and device where the remaining time is displayed on the digital display 139.

Figure 3:
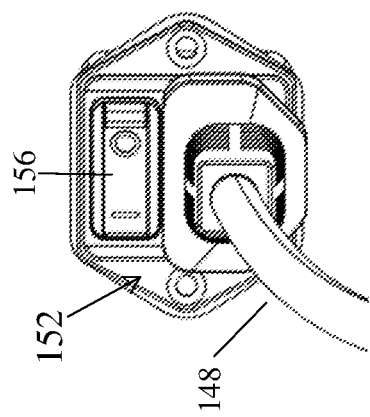
FIG. 3 is a view of the power inlet and a power cord of the photon therapy device, located at the chassis rear end on interior vertical wall of an electronic compartment, in accordance with an embodiment of the present disclosure.

FIG. 3 is a view of a power inlet 152 and its attached power cord 148. The power cord 148 cord when plugged into an electrical outlet provides power to the power inlet 152. The power inlet 152 contains a switch 156 to control electrical power to the device 100. In an exemplary embodiment, as illustrated in FIGS. 5 and 8, the power inlet 152 is located at the chassis underside near the rear end 172.

Figure 4:
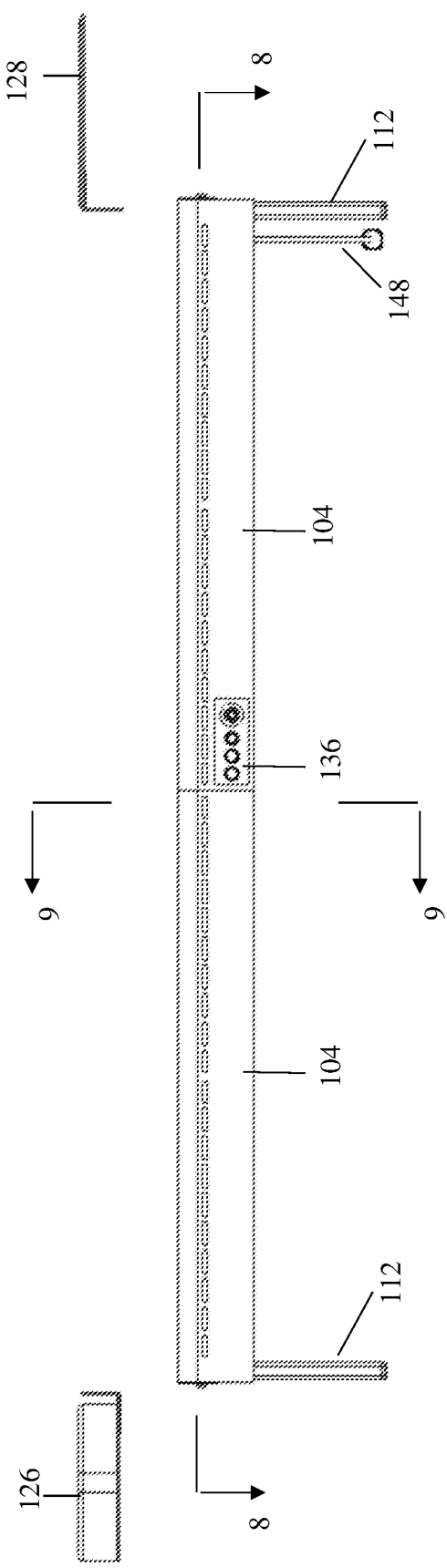
FIG. 4 is a side view of the partially disassembled device comprising the chassis separated from the removeable headrest and footrest of the photon therapy device in accordance with an embodiment of the present disclosure.
Figure 5:
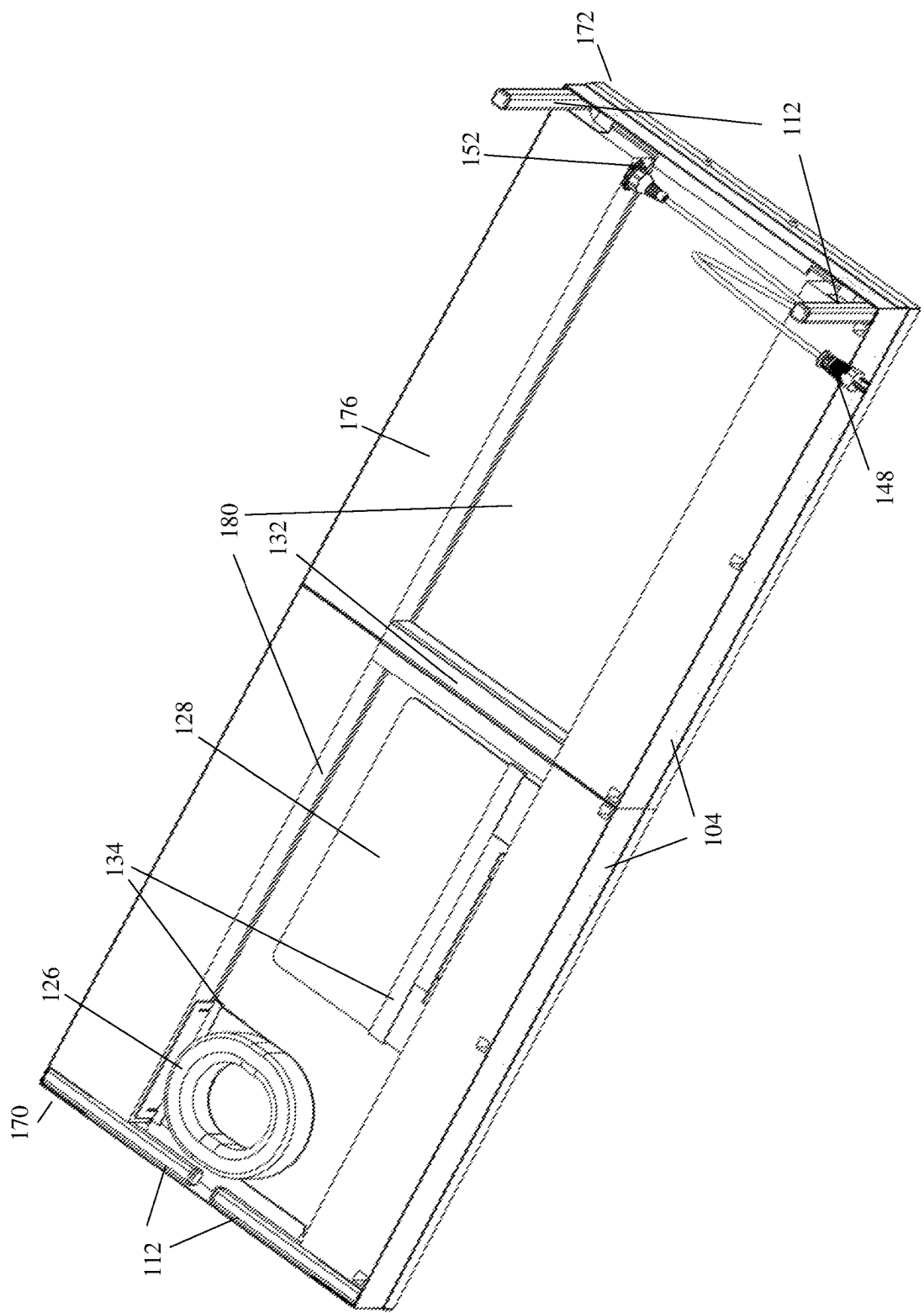
FIG. 5 is an underside view of the chassis with legs folded in, and with the headrest and footrest stowed within the photon therapy device in accordance with an embodiment of the present disclosure.

FIG. 4 and FIG. 5 are views of FIG. 1A, which is a two-piece chassis embodiment of the device 100, however the descriptions below apply to both FIGS. 1A and 1B except where noted.

FIG. 4 is an exploded side view of photon therapy device 100, which shows its modular capabilities as the headrest 126 and footrest 128 are depicted as removed from the chassis 104. The headrest 126 and footrest 128 attached to the chassis 104 provide improved comfort while extending the device length and thereby accommodating someone taller. The headrest 126 and footrest 128 are designed to be removed so that the device 100 may maintain its portability.

FIG. 5 is a perspective view of a bottom surface or underside 176 of the chassis 104 of the device 100, depicting how the resulting interior gap or cavity 180 of the device 100 can be used for storage of the headrest 126 and footrest 128 by utilizing elastic straps 134 to hold them in place. These modular components may be stored in this gap or cavity during transport, aiding in the portability of the device 100.

Upon the removal of the headrest 126 and the footrest 128, and folding of the legs 112, the device 100 is significantly shortened in length and height with only the chassis 104 left to contribute the greatest dimensions. In a two-piece chassis embodiment (e.g. FIG. 1A), at least one hinge 132 is also located on the underside 176 of the chassis 104 at the middle section so that the chassis folds inward in half to expose the two acrylic sheets 108 on the outside. In another two-piece chassis embodiment, not shown in drawings, the hinge 132 is replaced by an interlocking joint which enables the two chassis sections to be disconnected for disassembly rather than folded. Interlocking joints are well known to the skilled artisan (e.g. U.S. Pat. Ser. No. 10,281,108 B2 published May 27, 2019).

Figure 6:
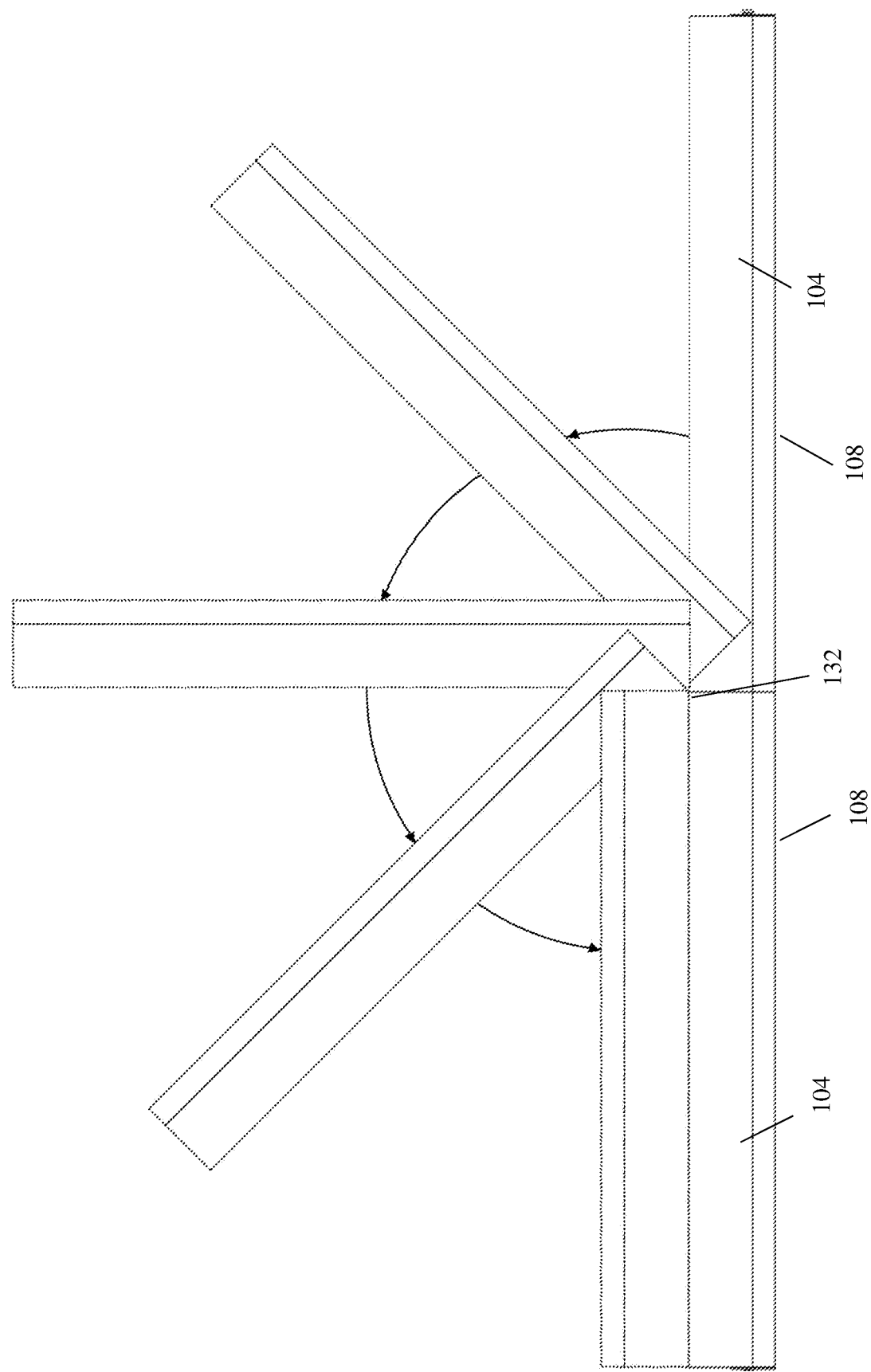
FIG. 6 is an upside down, side view of the photon therapy device demonstrating the method of folding the chassis in half after stowing the headrest and footrest and folding the legs.

FIG. 6, which applies to the two-piece chassis folding embodiments (e.g. FIG. 1A), is a side view of FIG. 5 illustrating the device 100 placed bottom side 176 up (e.g. after stowing the headrest and footrest), which depicts the functionality of the device 100 to fold via a hinge 132. FIG. 6 illustrates how two panels 108 of the chassis 104 begin at an angle of 180 degrees from one another and finish at an angle of 0 degrees.

One would take the two separate panels 108 of the chassis 104 and rotate them as depicted in FIG. 6 by utilizing the hinge 132, effectively folding chassis 104 in half. Folding the chassis 104 into a closed position with the headrest 126 the footrest 128 stowed inside along with the legs 112 folded would permit the chassis 104 to fit inside a carrying case, travel case, container, or item of luggage when the device 100 is to be transported.

In a two-piece chassis embodiment (e.g. FIG. 1A), the travel case 160 comprises dimensions that are less than or equal to 62 linear (length+width+height) inches (158 centimeters); and when the travel case 160 is packed with the photon therapy device 100, then it weighs less than or equal to 50 pounds (23 kilograms). These dimensions and weights meet major airline standard checked baggage restrictions.

In a one-piece chassis embodiment (e.g. FIG. 1B), the travel case 165 (e.g. FIG. 7B) is substantially rectangular shaped, and comprises dimensions that are less than or equal to about 126 linear (length+width+height) inches (320 centimeters); and when the travel case 165 is packed with the photon therapy device, then it weighs less than or equal to about 100 pounds (45 kilograms). These dimensions and weights meet major airline oversized/overweight checked baggage restrictions. Travel case 165 comprises a suitcase appearance with a carry handle 162, and at least one latch 164 to lock the case closed.

Figure 7A:
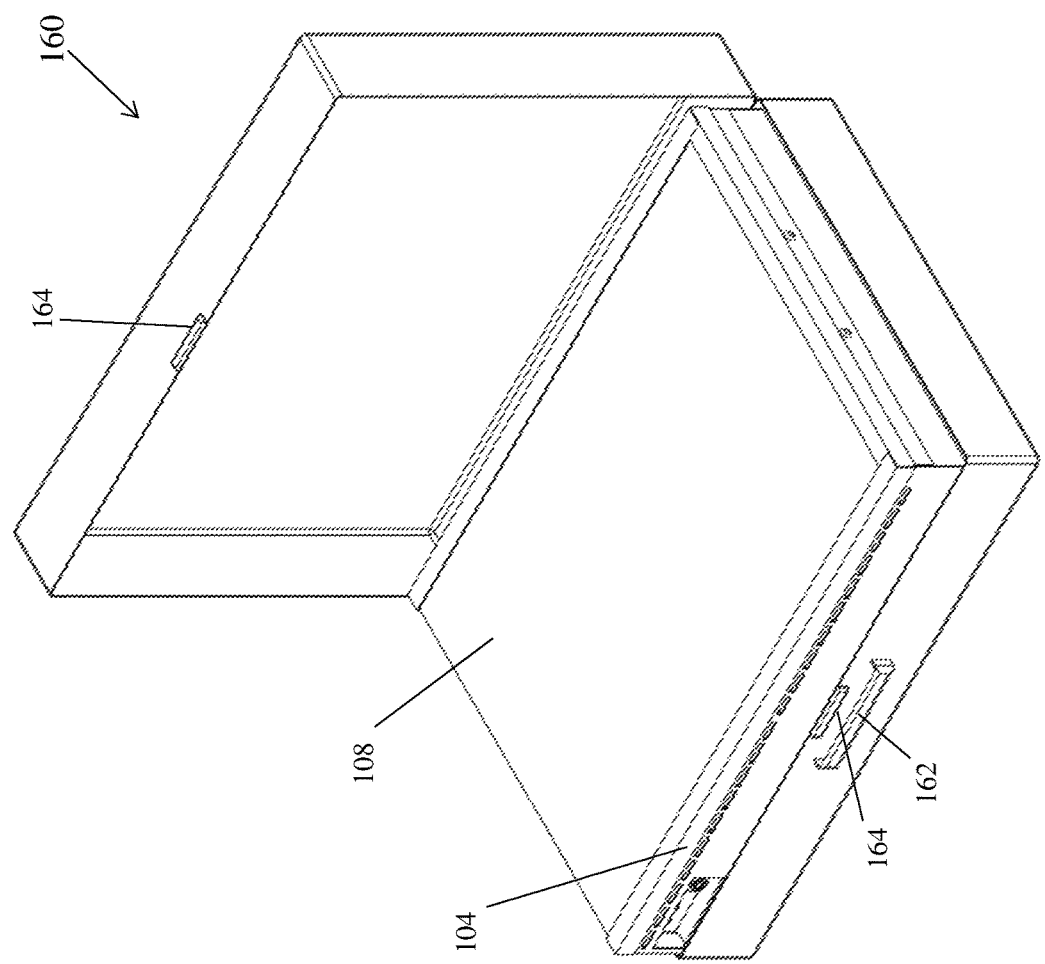
FIG. 7A is a view of the photon therapy device in FIG. 1A in a folded or disassembled position and stored in an airline compliant checked travel briefcase in accordance with an embodiment of the present disclosure.

FIG. 7A is a perspective view of a two-piece chassis embodiment (e.g. FIG. 1A) of device 100 folded or disassembled and stacked. The device 100 may be inserted into a carrying case, travel case, container, or item of luggage 160, thus demonstrating the portability of the device 100. In an embodiment, the travel case 160 comprises a suitcase appearance with a carry handle 162, and at least one latch 164 to lock the case closed.

Figure 7B:
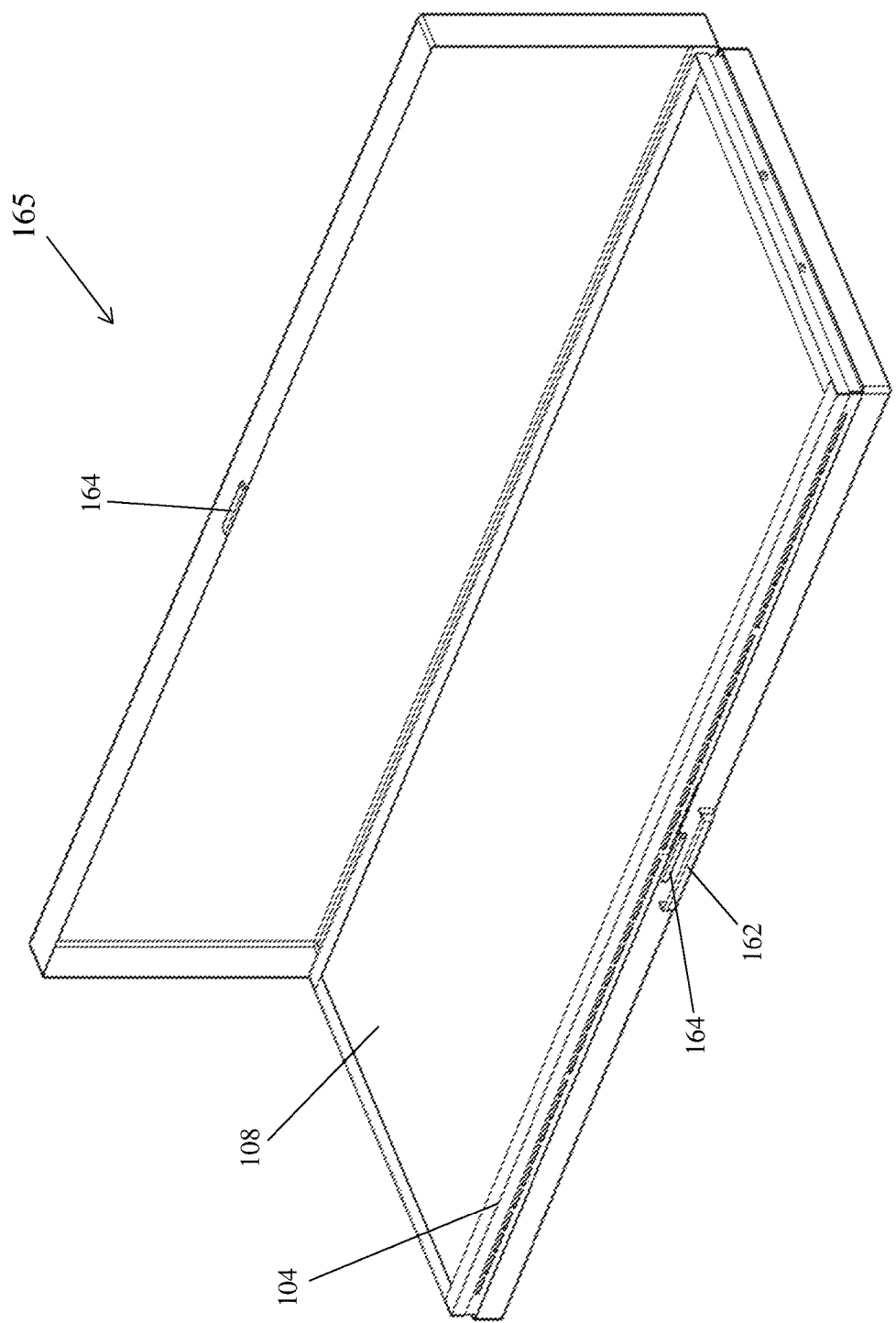
FIG. 7B is a view of the photon therapy device in FIG. 1B stored in an airline compliant checked travel case in accordance with an embodiment of the present disclosure.

FIG. 7B is a perspective view of a one-piece chassis embodiment (e.g. FIG. 1B) of device 100 inserted into a carrying case 165, thus demonstrating the portability of the device 100. In an embodiment, the travel case 165 comprises a suitcase appearance with a carry handle 162, and at least one latch 164 to lock the case closed.

Figure 9:
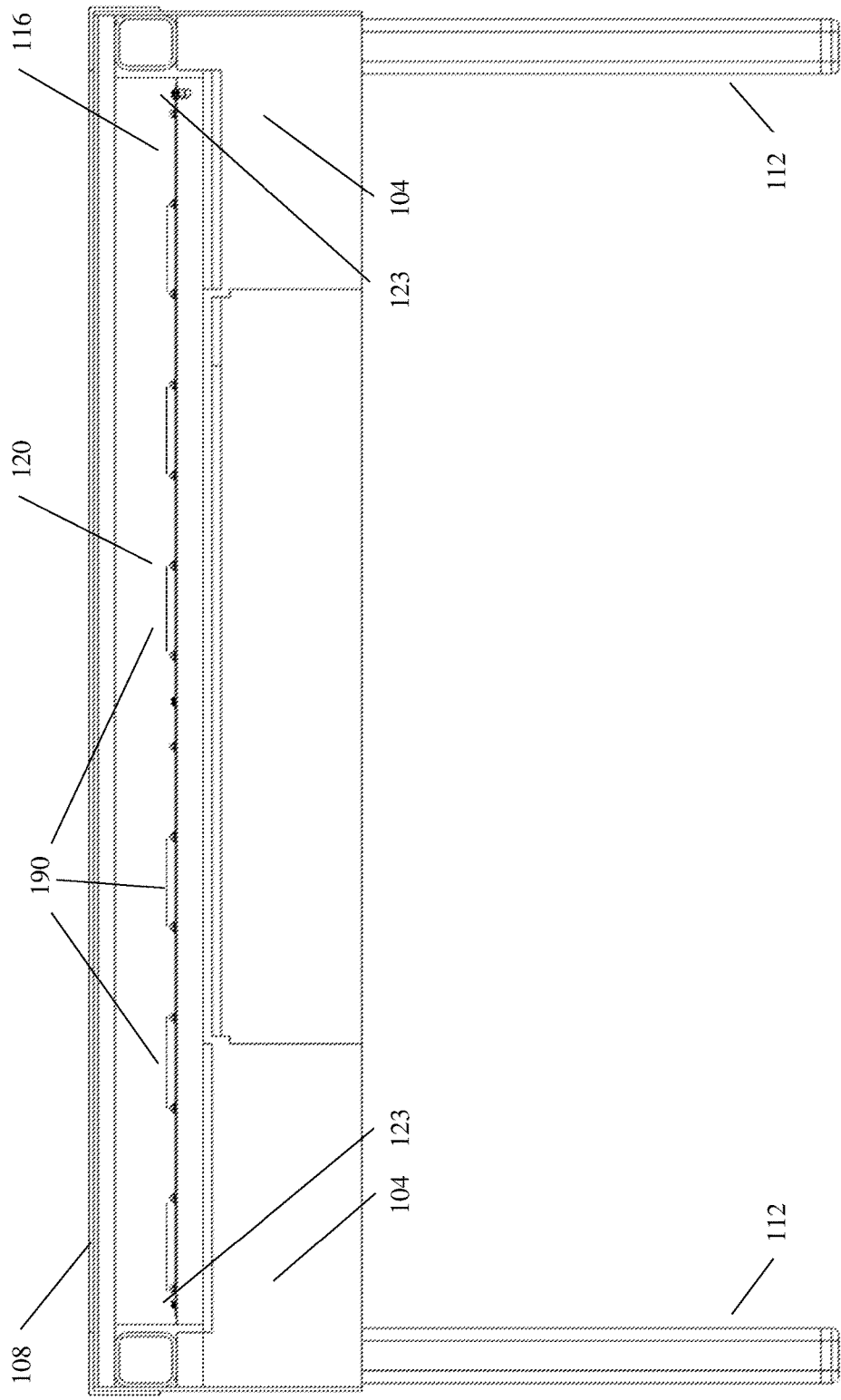
FIG. 9 is a vertical cross-sectional view of FIG. 4 taken along line 9-9, illustrating a cutaway view of the chassis.

FIG. 8 is a longitudinal cross-sectional view taken along line 8-8 of FIG. 4's chassis, which shows the electronic components that are comprised within device 100. The Driver PCBs 117 provide string amperage (e.g., see dotted lines 190, FIG. 1 middle array 116, and FIG. 9) and voltage to the LED Array PCBs (e.g. FIG. 1, 116), thermal sensors 123, and the blowers 122 to cool the LEDs 120. Each Driver PCB 117, controls two end-to-end aligned LED Array PCBs 116. The Control PCB 118 provides signals to the Driver PCBs 117 using buttons on the control panel 136 for light wavelengths and mode (continuous or pulse). In one embodiment, the Control PCB 118, contains a microcontroller 124 which enables the buttons and digital display on the FIG. 2B and FIG. 2C control panels. The Control PCB 118 also provides power to the Driver PCBs 117 from the power supply unit 121. The Control PCB 118 also contains a non-adjustable internal (not displayed) timer 119 that prevents over-exposure, which powers down the device (e.g. after 30 minutes in an embodiment). The Control PCB 118 also provides a power disable signal to the power supply unit 121 when the emergency stop button 140 is pressed on the control panel 136. The power inlet 152 provides power to the power supply unit 121."

Method of Treatment

After device 100 setup and upon selection of the desired light wavelengths (e.g. red at 660 nm and infrared at 850 nm) and mode (pulsed or continuous wave) via switches on the control panel, one lays down on the device bed to undergo photon therapy for a specific duration of time. Photon research studies provide a vast and increasing amount of therapeutic protocols to utilize with this device. The research protocols typically define the wavelengths, the mode, and the fluence (dosage) for a given indication of use (ex. increase endurance, decrease inflammation, adjunct to weight loss, etc.). Given the fluence (dosage), which is measured in $J/cm^2$, one can determine the duration of treatment based on the irradiance (photon power density) of this device which, in an embodiment, is targeted to provide between 25 $mW/cm^2$ and 50 $mW/cm^2$ depending on configuration. The photon therapy device 100 also comprises an internal timer 119 that shuts down the device, after 30 minutes in an embodiment, to prevent overexposure. In an embodiment, one utilizes their smartphones (listening to music, texting, etc.) during treatment and therefore would use the phone timer to set and track session duration alarms. In another embodiment, control panel FIG. 2B, 136 further comprises a digital timer with pushbuttons to add time and start timer. In yet another embodiment, one would use the photon therapy mobile device application control panel FIG. 2C, 136 for controlling session durations.

A common athletic PBMT protocol, which targets muscle cell types, prescribes daily therapy using continuous-wave red (660 nm) and IR (850 nm) wavelengths at fluences (dosages) ranging from 10 to 50 $J/cm^2$. This device is targeted to deliver an irradiance levels (photon power densities) of between 25 $mW/cm^2$ and 50 $mW/cm^2$ depending on wavelengths and mode selected. With an output of 25 $mW/cm^2$, one would need to spend 10 minutes per prone and supine positions to obtain a fluence (dose) of 15 $J/cm^2$ (Joules=Watts×seconds), which is both effective and efficient.

The device also supports PBMT protocols that may reduce complications from COVID-19, the infectious disease caused by Severe Acute Respiratory Syndrome Coronavirus 2 (SARS-CoV-2). Pneumonia with acute respiratory distress (ARDS) is one of the more severe complications, with symptoms including pulmonary inflammation, airway edema, and lung fibrosis. Numerous PBMT rodent studies have demonstrated significant reductions in pulmonary inflammation, airway edema, and lung fibrosis in induced models of asthma and ARDS with effective fluences of 1 $J/cm^2$ to 9 $J/cm^2$ using both red and IR wavelengths (Rigonato-Oliveira et al., 2019 [6]), (Oliveira et al., 2014 [7]), (Brochetti et al., 2017 [8]). There have also been several human studies utilizing PBMT for treatment of both pneumonia and bronchial asthma with varying protocols that have significantly improved patient outcomes with faster recovery times, reduced inflammation, and improved biomarkers (Lutai et al., 2001 [9]), (Ostronosova et al., 2006 [10]), (Milojević et al., 2003 [11]), (Dabbous et al., 2017 [12]). Further studies are warranted to determine the optimal protocol including fluences (dosage), wavelengths, device mode, and treatment frequency for ARDS.

Method of use of device: open case and assemble device; select wavelengths of light and mode, set timer on mobile phone (not included), or on the control panel, or via the device mobile phone application, lay on chassis top surface; when timer expires turn over (from prone to supine or vice-versa), set timer, when timer expires device turns off (in device equipped with timers) or manually turn off (in device without timer), after; clean top surface with antibiotic cleaner and dry, disassemble, and pack the device in the travel case.

The device has numerous safety related features incorporated into the design. The safety stop switch 140 on the control panel 136 as illustrated in FIGS. 2A and 2B enables the quick shut down of the main power delivered to the electronics from the power supply unit (PCBs and blowers). The device also has an internal timer 119 which shuts off the device (e.g. after 30 minutes of use in an embodiment) to prevent over-exposure. The LED Array PCBs 116 have at least one thermal sensor 123 that shuts down the LEDs 120 when their temperature exceeds 75 degrees C. In the exemplified embodiment of FIG. 1, each PCB 116, comprises a thermal sensor 123 on each of the board's four corners, and another in the board middle. As such, in this embodiment, device 100 comprises up to 20 thermal sensors 123.

The Driver PCBs 117 also have open-LED protection, short-circuit protection, as well as undervoltage and overvoltage lockouts for the LEDs 120 on the LED Array PCBs 116, which all assist in ensuring the electronics operate within specifications. The device has been designed to be compliant with EMI (electro-magnetic interference) conducted and radiated emission standards and immunity standards per IEC (International Electrotechnical Commission) 60601-1-2:2014 Edition 4 medical electrical equipment standards.

Mobile Application

Figure 10:
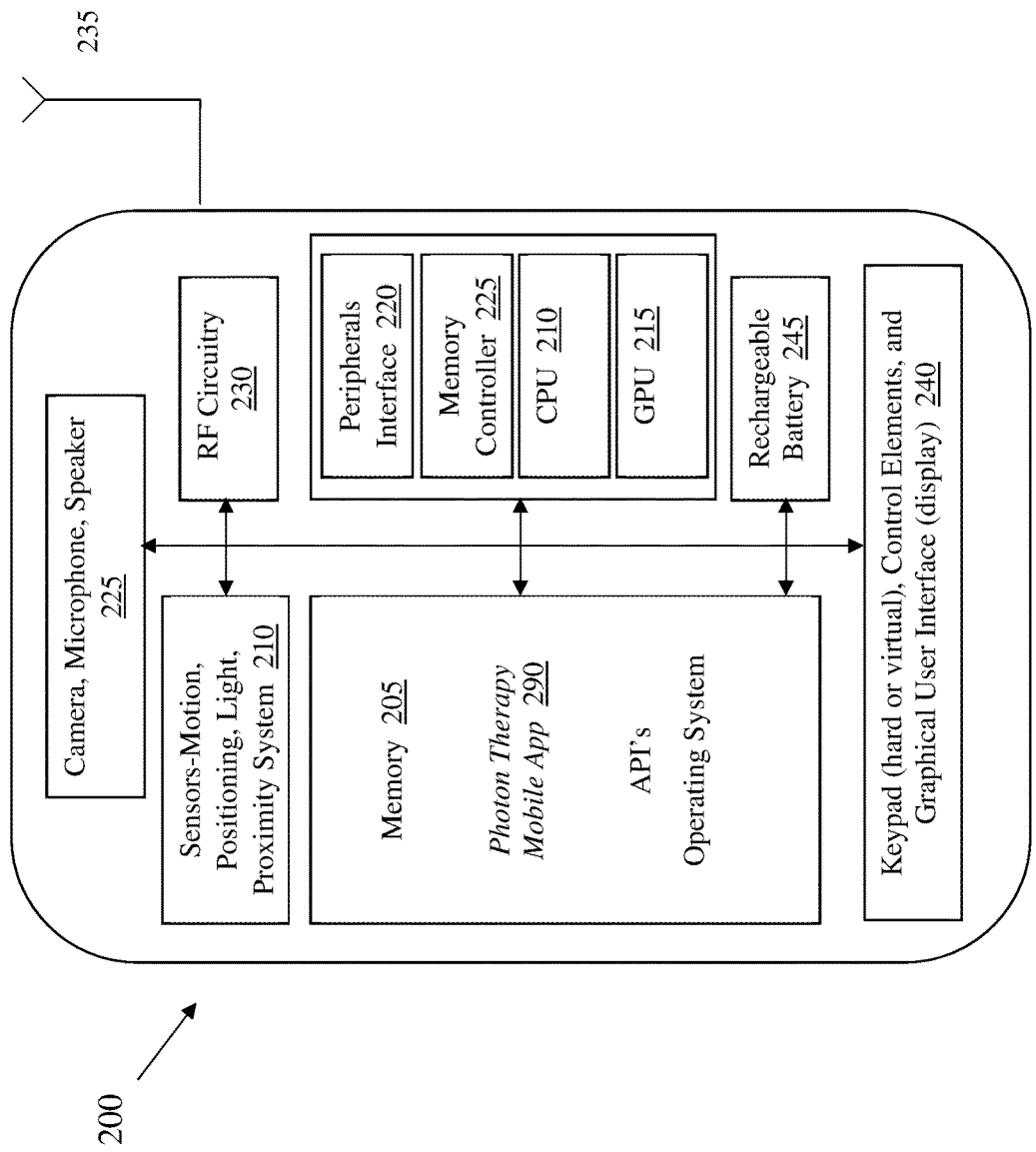
FIG. 10 is a block diagram of a user mobile electronic device (e.g. a smartphone) having installed thereon, or accessible via a wireless network, the non-transitory computer readable storage media (i.e. the mobile application) used to control the photon therapy device.

As illustrated in FIG. 10, the system of the present invention further comprises a photon therapy mobile application 290 installed on a user's electronic computing device 200 (e.g. a tablet, smartphone, etc.) or accessible via a website from (e.g. a laptop, desktop, PDA, etc.) to control the operation of the photon therapy device 100.

The mobile application 290 comprises a computer program product, comprising a non-transitory machine-readable storage medium having encoded therein executable code of one or more software programs, wherein the one or more software programs when executed by at least one processor on a user electronic computing device performs the following steps of: remotely controlling the operation of the photon therapy device via wirelessly (e.g. Bluetooth chip or wireless chip) connecting to the control panel (FIG. 2C, 136). The mobile phone application 290 has the same functionality as the FIG. 2B control panel (hardware) as stated supra.

In an embodiment, the system 100 further comprises a non-transitory computer readable medium storing computer executable code, wherein the computer executable code, when executed by a processor on the mobile electronic computing device 200, is configured to: receive, transmit and display information between said mobile device 200 and said chassis for controlling the operation of the system, comprising for example: treatment time duration; pulsed or continuous mode; and primary (e.g. red light) wavelength, secondary (e.g. IR) wavelength, or both.

An exemplary illustrated in FIG. 10, the user electronic computing device 200 (e.g. smartphone, laptop, tablet, etc.) further comprises the following components: memory 205 with an operating system (e.g. Android®); central processing unit 210; graphical processing unit 215; peripherals interface 220 to facilitate device 100 monitoring; camera, microphone and speaker communications 225; motion, positioning, light, and proximity system 210 for use by operating system, API's, and applications; radio frequency (RF) subsystem 230 with antenna 235 to wirelessly transmit instructions and data, or other wireless communications between device 100 and 200; one or more means of inputting user data 240, e.g. using a touchscreen or pointer (e.g. keypad-hard or virtual; control elements; GUI; etc.); and a rechargeable battery 245.

Memory 205 has installed therein the photon therapy mobile application/module 290 of the present invention, which may further comprise the use of one or more application program interfaces (API's). The memory 205 or other data storage unit (e.g. a cloud account) stores data, such as history of operation and treatment sessions, security alerts (e.g. overheating of device 100 and automatic shutoff), instructions from health care providers, etc.

Additionally, memory 205 (which may include one or more computer readable storage mediums) also comprises high-speed random-access memory and may also include non-volatile memory, such as one or more magnetic disk storage devices, flash memory devices, or other non-volatile solid-state memory devices. Access to memory 205 by other components of the device 200, such as the CPU 210, may be controlled by a memory controller 225.

The RF (radio frequency) subsystem 230 receives and sends RF signals by converting electrical signals to/from electromagnetic signals and communicates with communications networks and other communications devices via the electromagnetic signals. The RF subsystem comprises well-known circuitry for performing these functions, including but not limited to a Bluetooth chip, a wireless chip, an antenna system, an RF transceiver, one or more amplifiers, a tuner, one or more oscillators, a digital signal processor, a CODEC chipset, a subscriber identity module (SIM) card, memory, and so forth. The RF subsystem communicates wirelessly via WiFi (e.g. 802.11ax) or wireless broadband (e.g. LTE, GSM/EDGE, CDMA) with the Internet (e.g. public network) or an intranet (e.g. private home or business network). The RF subsystem also communicates wirelessly via Bluetooth (e.g. v5.0) to other devices such as printers and headphones.

Conclusion

It will be appreciated that the methods and compositions and compounds of the present disclosure can be incorporated in the form of a variety of embodiments, only a few of which are disclosed herein. It will also be apparent for the expert skilled in the field that other embodiments exist and do not depart from the spirit of the invention. Thus, the described embodiments are illustrative and should not be construed as restrictive.

Accordingly, the preceding exemplifications merely illustrate the principles of the various embodiments. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the various embodiments, therefore, is not intended to be limited to the exemplary embodiments shown and described herein.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described.

The term "about" as used herein refers to a value within 10% of the underlying parameter (i.e., plus or minus 5%), and use of the term "about" at the beginning of a string of values modifies each of the values (i.e., "about 1, 2 and 3" refers to about 1, about 2 and about 3). Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

As used herein, the term "substantially" refers to approximately the same shape as stated, and recognizable by one of ordinary skill in the art.

Trademarks: the product names used in this document are for identification purposes only; and are the property of their respective owners.

LIST OF REFERENCES CITED

[1] Zein, R. et al. (2018) Review of light parameters and photobiomodulation efficacy: dive into complexity. *J. Biomed. Opt.*, 23(12), 120901: 1-17.
[2] Hamblin M R. (2019) Photobiomodulation for Alzheimer's Disease: Has the Light Dawned? *Photonics.* 6(3):77.
[3] Welch, D. et al. (2018) Far-UVC light: A new tool to control the spread of airborne-mediated microbial diseases, *Scientific Reports,* 8: 2752.
[4] Wang Y. et al. (2017) Antimicrobial blue light inactivation of pathogenic microbes: State of the art. Drug Resist Update. 33-35:1-22.
[5] Schuit, M. et al. (2020) The Influence of Simulated Sunlight on the Inactivation of Influenza Virus in Aerosols. *The Journal of Infectious Diseases,* 221(3): 372-378. Abstract
[6] Rigonato-Oliveira, N C. et al. (2019) Effect of Low-Level Laser Therapy (LLLT) in Pulmonary Inflammation in Asthma Induced by House Dust Mite (HDM). Dosimetry Study. *Int J Inflam.* 3945496: 1-12.
[7] Oliveira M C Jr, et al. (2014) Low level laser therapy reduces acute lung inflammation in a model of pulmonary and extrapulmonary LPS-induced. ARDS. *J Photochem Photobiol B.* 134:57-63. Abstract
[8] Brochetti, R. A. et al. (2017) Photobiomodulation therapy improves both inflammatory and fibrotic parameters in experimental model of lung fibrosis in mice. *Lasers Med Sci,* 32:1825-1834.
[9] Lutai, A. V. (2001) Laser therapy of elderly patients with pneumonia. *Vopr Kurortol Fizioter Lech Fiz Kult* 3: 15-18. Abstract
[10] Ostronosova N S. (2006) Outpatient Use of Laser Therapy in Bronchial Asthma. *Ter Arkh.* 78(3):41-44. Abstract
[11] Milojević M. et al. (2003) Low power laser biostimulation in the treatment of bronchial asthma. *Med Pregl.* 56(9-10):413-418. Abstract
[12] Dabbous O A. et al. (2017) Evaluation of the improvement effect of laser acupuncture biostimulation in asthmatic children by exhaled inflammatory biomarker level of nitric oxide. *Lasers Med Sci.* 32(1): 53-59. Abstract

What is claimed is:

1. A portable table housing a therapeutic photon therapy system, comprising:
   a) a substantially hollow chassis consisting of,
      one or two flat acrylic sheet(s), aligned end-to-end, positioned for a patient to lie down upon;
      four light-emitting diodes (LEDs) array printed circuit boards (PCBs) positioned in parallel beneath the flat acrylic sheet(s), wherein each LED array PCB houses a plurality of LEDs configured to emit photons at a plurality of light wavelengths that pass through the acrylic sheet(s) and into the patient;
      two driver PCBs, each driving two of the LED arrays PCBs, wherein the LEDs are arranged in strings and configured to provide each string a specific amperage and voltage to produce a level of therapeutic irradiance;
      four LED blowers, each positioned beneath one of the LED array PCBs for cooling the LEDs;
      a control panel connected to a control PCB for entering and executing patient therapeutic or preventive photon treatment protocols for one or more of the following: to reduce inflammation; to inactivate pathogens in a patient; to facilitate endurance, strength, and recovery in an athlete; and wherein the control panel is configured to receive user input for the treatment protocol comprising: a selection of light wavelengths, and a mode of pulsed or continuous wavelengths;
      a power supply unit able to transmit current and/or voltage from a wall outlet to the control PCB to the two driver PCBs;
      one to five thermal sensors positioned within each LED array PCB, able to shut off the LEDs when the LED array PCB temperature exceeds a safety level to prevent overheating;
      a hollow inner cavity within the hollow chassis, wherein the headrest and footrest are detachable from the hollow chassis and able to be stored inside the chassis hollow inner cavity when the portable table is not in use;
   b) a plurality of foldable legs;
   c) wherein the legs are able to be folded into the chassis when the portable table is not in use;
   d) a detachable headrest extending from an end of the chassis, positioned to support a patient's head in both a supine and a prone position; and
   e) a detachable footrest extending from an end of the chassis.

2. The system of claim 1, further comprising one or more safety features consisting of:
   a) an internal timer positioned within the control PCB, able to shut off the system after a set time duration to prevent over-exposure;

b) an emergency stop button on the control panel that disables the power supply unit;

c) an electrical circuitry within the driver PCB configured to prevent overvoltage, undervoltage, and short circuits in the LED array PCB; and/or d) wherein the system is compliant with electro-magnetic interference (EMI) conducted and radiated emission standards and immunity standards for a photon therapy device to treat muscles and joints, increase blood circulation, decrease inflammation, and inactivate pathogens, in environments comprising: a home, a hotel room, a sports team facility, a medical facility, and a hospital.

3. The system of claim 1, wherein the hollow chassis consists of two flat acrylic sheets able to fold with the chassis in half to fit within a travel briefcase that meets an airline standard checked baggage requirements comprising less than or equal to 62 linear inches in total dimensions, and a maximum of 50 pounds.

4. The system of claim 1, wherein the hollow chassis consists of one flat acrylic sheet, and the chassis is stored in a substantially rectangular shaped travel case that meets an airline oversized/overweight checked baggage requirements comprising less than or equal to 126 linear inches in total dimensions, and a maximum of 100 pounds.

5. The system of claim 1, wherein the LEDs emit therapeutic wavelengths between about 200 nm ultraviolet to about 1064 nm infrared, and at a therapeutic irradiance level between about 25 mW/cm$^2$ to about 100 mW/cm$^2$.

6. The system of claim 5, wherein the LEDs are arranged in an array pattern to ensure delivery of a consistent irradiance and dosage.

7. The system of claim 1, wherein the control panel further comprises two depress-able buttons for three operation options comprising: a primary wavelength, a secondary wavelength, or both the primary and the secondary wavelength.

8. The system of claim 7, wherein the control panel further comprises a switch to enable one to select between pulsed or continuous wavelengths.

9. The system of claim 7, wherein the control panel further comprises a timer button to set the duration of treatment; and a digital display indicating a treatment time.

10. The system of claim 1, wherein the system further comprises a non-transitory computer readable medium storing computer executable code, wherein the computer executable code, when executed by a processor on a mobile electronic computing device, is configured to: receive, transmit and display information between said mobile device and said chassis for controlling the operation of the system, comprising: a treatment time duration; a pulsed or continuous mode; and administration of a primary wavelength, a secondary wavelength, or both.

11. A method of treatment or prevention of a medical condition requiring photon therapy, utilizing the portable table housing a therapeutic photon therapy system of claim 1, comprising:

a) opening a travel case or briefcase, removing from, and assembling the portable table housing the therapeutic photon therapy system, b) selecting on the control panel the treatment protocols;

c) activating the power for the plurality of LEDs to on and lying down on the chassis top surface;

d) when the duration of treatment expires, the system automatically or the patient manually turns the power off; and e) cleaning the chassis top surface, disassembling and packing the portable photon therapy system in the travel case or briefcase.

12. The method of claim 11, wherein the system further comprises one or more safety features consisting of:

a) an internal timer positioned within the control PCB, able to shut off the system after a set time duration to prevent over-exposure;

b) an emergency stop button on the control panel that disables the power supply unit;

c) an electrical circuitry within the driver PCB configured to prevent overvoltage, undervoltage, and short circuits in the LED array PCB; and/or d) wherein the system is compliant with electro-magnetic interference (EMI) conducted and radiated emission standards and immunity standards for a photon therapy device to treat muscles and joints, increase blood circulation, decrease inflammation, and inactivate pathogens, in environments comprising: a home, a hotel room, a sports team facility, a medical facility, and a hospital.

13. The method of claim 11, wherein the hollow chassis consists of two acrylic sheets able to fold with the chassis in half to fit within a travel briefcase that is able to meet an airline standard checked baggage requirements comprising 62 linear inches in total dimensions, and a maximum of 50 pounds.

14. The method of claim 11, wherein the hollow chassis consists of one acrylic sheet, and the chassis is stored in a substantially rectangular shaped travel case meeting an airline oversized/overweight checked baggage requirements comprising less than or equal to 126 linear inches in total dimensions, and a maximum of 100 pounds.

15. The method of claim 11, wherein the LEDs emit therapeutic wavelengths between about 200 nm ultraviolet to about 1064 nm infrared, and at a therapeutic irradiance level between about 25 mW/cm$^2$ to about 100 mW/cm$^2$.

16. The method of claim 15, wherein the LEDs are arranged in an array pattern to ensure delivery of a consistent irradiance and dosage.

17. The method of claim 11, wherein the control panel further comprises two depress-able buttons for three operation options comprising: a primary wavelength, a secondary wavelength, or both the primary and the secondary wavelength.

18. The method of claim 17, wherein the control panel further comprises a switch to enable one to select between pulsed or continuous wavelengths.

19. The method of claim 17, wherein the control panel further comprises a timer button to set the duration of treatment; and a digital display indicating a treatment time.

20. The method of claim 11, wherein the system further comprises a non-transitory computer readable medium storing computer executable code, wherein the computer executable code, when executed by a processor on a mobile electronic computing device, is configured to: receive, transmit and display information between said mobile device and said chassis for controlling the operation of the system, comprising: a treatment time duration; a pulsed or continuous mode; and administration of a primary wavelength, a secondary wavelength, or both.

* * * * *